US009623126B2

(12) United States Patent
Weissleder et al.

(10) Patent No.: US 9,623,126 B2
(45) Date of Patent: Apr. 18, 2017

(54) MAGNETIC NANOPARTICLES

(71) Applicant: The General Hospital Corporation, Boston, MA (US)

(72) Inventors: Ralph Weissleder, Peabody, MA (US); Hakho Lee, Acton, MA (US); Tae-Jong Yoon, Yongin (KR)

(73) Assignee: The General Hospital Corporation, Boston, MA (US)

( * ) Notice: Subject to any disclaimer, the term of this patent is extended or adjusted under 35 U.S.C. 154(b) by 273 days.

(21) Appl. No.: 14/593,293

(22) Filed: Jan. 9, 2015

(65) Prior Publication Data

US 2015/0258222 A1 Sep. 17, 2015

Related U.S. Application Data

(62) Division of application No. 13/699,378, filed as application No. PCT/US2011/038143 on May 26, 2011, now Pat. No. 8,945,628.

(60) Provisional application No. 61/348,561, filed on May 26, 2010.

(51) Int. Cl.
| | | |
|---|---|---|
| *A61K 9/14* | (2006.01) | |
| *A61K 49/18* | (2006.01) | |
| *A61K 9/50* | (2006.01) | |
| *A61K 9/51* | (2006.01) | |
| *A61K 33/24* | (2006.01) | |
| *A61K 33/26* | (2006.01) | |
| *A61K 33/30* | (2006.01) | |
| *A61K 41/00* | (2006.01) | |
| *A61N 2/02* | (2006.01) | |
| *B22F 1/02* | (2006.01) | |
| *A61K 49/08* | (2006.01) | |
| *A61K 49/10* | (2006.01) | |
| *A61K 49/12* | (2006.01) | |

(52) U.S. Cl.
CPC ........ *A61K 49/1824* (2013.01); *A61K 9/5094* (2013.01); *A61K 9/5115* (2013.01); *A61K 33/24* (2013.01); *A61K 33/26* (2013.01); *A61K 33/30* (2013.01); *A61K 41/0052* (2013.01); *A61K 49/08* (2013.01); *A61K 49/10* (2013.01); *A61K 49/126* (2013.01); *A61K 49/183* (2013.01); *A61K 49/1827* (2013.01); *A61K 49/1836* (2013.01); *A61N 2/02* (2013.01); *B22F 1/025* (2013.01); *A61K 2800/47* (2013.01)

(58) Field of Classification Search
CPC ................................................. A61K 2800/47
See application file for complete search history.

(56) References Cited

U.S. PATENT DOCUMENTS

| | | | |
|---|---|---|---|
| 5,492,814 A | 2/1996 | Weissleder | |
| 5,736,349 A | 4/1998 | Sasaki | |
| 5,766,572 A | 6/1998 | Hasegawa | |
| 6,203,778 B1 | 3/2001 | Brasch | |
| 6,818,199 B1 | 11/2004 | Hainfeld | |
| 7,635,734 B2 | 12/2009 | Alferiev | |
| 2003/0092029 A1 | 5/2003 | Josephson | |
| 2003/0124194 A1 | 7/2003 | Gaw | |
| 2006/0068203 A1 | 3/2006 | Ying | |
| 2006/0177660 A1* | 8/2006 | Kumar et al. | 428/403 |
| 2006/0225535 A1 | 10/2006 | Mainwaring | |
| 2006/0269965 A1 | 11/2006 | Josephson | |
| 2008/0187595 A1 | 8/2008 | Jordan | |
| 2009/0004475 A1 | 1/2009 | Sadaka et al. | |
| 2009/0043198 A1* | 2/2009 | Milner et al. | 600/437 |
| 2009/0324494 A1 | 12/2009 | Ham | |
| 2010/0303716 A1* | 12/2010 | Jin et al. | 424/1.11 |

FOREIGN PATENT DOCUMENTS

| | | |
|---|---|---|
| CN | 1979699 | 6/2007 |
| WO | 00/61191 | 5/2001 |
| WO | 2006/102377 | 9/2006 |
| WO | 2009/031859 | 3/2009 |

OTHER PUBLICATIONS

Authorized officer Lantes M. Vazquez, Supplementary EP Search Report in EP 11 78 7417 mailed Feb. 5, 2014, 5 pages.
Authorized officer Sun Hwa Lee, International Search Report and Written Opinion in PCT/US2011/038143 mailed Jan. 19, 2012, 11 pages.
Authorized officer Xinqin Feng, First Office Action in CN 201180036546.7 mailed Oct. 30, 2013, 27 pages.
Farrell et al., "Preparation and Characterization of Monodisperse Fe Nanoparticles," J. Phys. Chem. B 2003, 107:11022-11030, 9 pages.
Gossuin et al., "Magnetic resonance relaxation properties of superparagmagnetic particles," WIREs Nanmed. Nanobiotech. 2009, 1:299-310, 12 pages.
Huber, "Synthesis, Properties, and Applications of Iron Nanoparticles," Small 2005, 1(5):482-501, 20 pages.
International Search Report and Written Opinion mailed Jan. 19, 2012 from International Application No. PCT/US2011/038143, 11 pgs.
Lee et al., "Ultrasensitive detection of bacteria using core-shell nanoparticles and an NMR-filter system" and Supporting Information, Angewandte Chemie, 121(31):5767-5770 (Jul. 20, 2009).
Lee et al., "Artificially engineered magnetic nanoparticles for ultra-sensitive molecular imaging," Nature Medicine 13(1):95-99, 2007, 5 pages.
Lee et al., "Chip-NMR biosensor for detection and molecular analysis of cells," Nat. Med. 14, pp. 869-874, 2008.
Lee et al., "Rapid detection and profiling of cancer cells in fine-needle aspirates," PNAS 106(30):12459-12464, 2009, 8 pages.
Lee et al., "Ultrasensitive detection of bacteria using core-shell nanoparticles and an NMR-filter system," and Supporting Information, Angew. Chem. Int. Ed. 48:5657-5660, 2009, 19 pages.

(Continued)

*Primary Examiner* — Paul Dickinson
(74) *Attorney, Agent, or Firm* — Fish & Richardson P.C.

(57) ABSTRACT

A magnetic nanoparticle includes a magnetic core and a superparamagnetic outer shell, in which the outer shell enhances magnetic properties of the nanoparticle. The enhanced magnetic properties of the magnetic nanoparticle allow for highly sensitive detection as well as diminished non-specific aggregation of nanoparticles.

11 Claims, 9 Drawing Sheets

(56) References Cited

OTHER PUBLICATIONS

Linderoth et al., "Oxidation of nanometer-sized iron particles," Journal of Materials Science 1995, 30:3142-3148, 7 pages.
Peng et al., "Synthesis and Stabilization of Monodisperse Fe Nanoparticles," J. Am. Chem. Soc. 2006, 128:10676-10677, 2 pages.
Perez et al., "Magnetic relaxation switches capable of sensing molecular interactions," Nat. Biotechnol., 2002, 20:816-820, 5 pages.
Qiang et al., "Iron/iron oxide core-shell nanoclusters for biomedical applications," J. Nanopart. Res. 8:489-496, 2006, 8 pages.
Shao et al., "Control of Iron Nanoparticles Size and Shape by Thermal Decomposition Method," IEEE Trans. Magn. 41(10):3388-3390, 2005, 3 pages.
Sun et al., "Monodisperse MFeO (M=Fe, Co, Mn) Nanoparticles," J. Am. Chem. Soc., 2004, 126(1):273-279, 8 pages.

\* cited by examiner

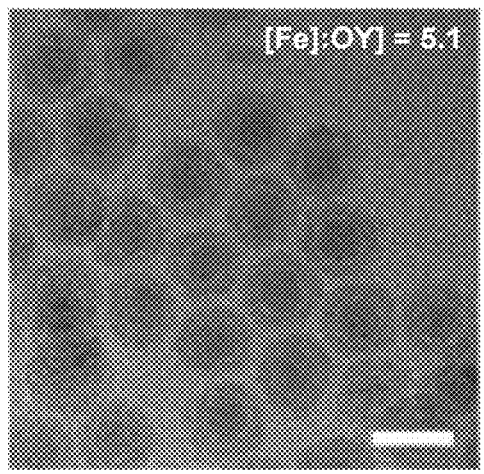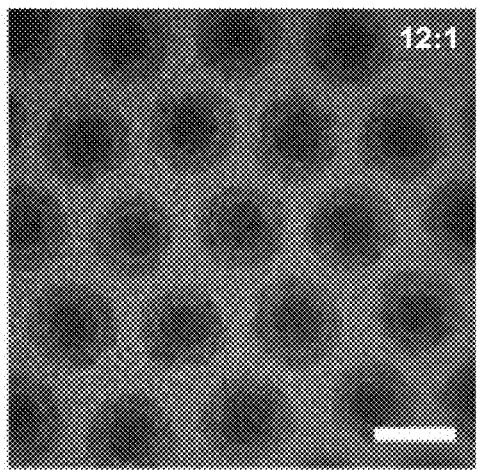
FIG. 3A          FIG. 3B
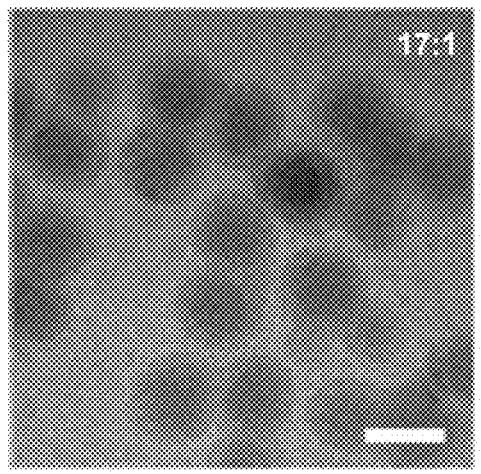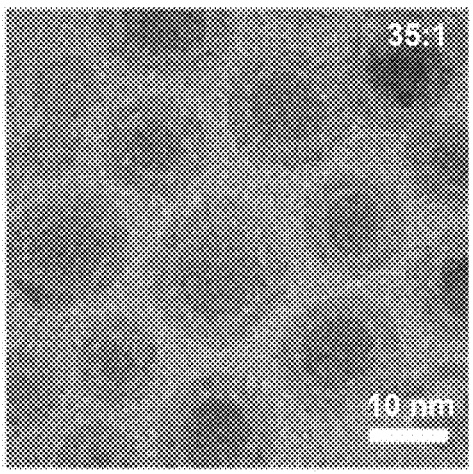
FIG. 3C          FIG. 3D

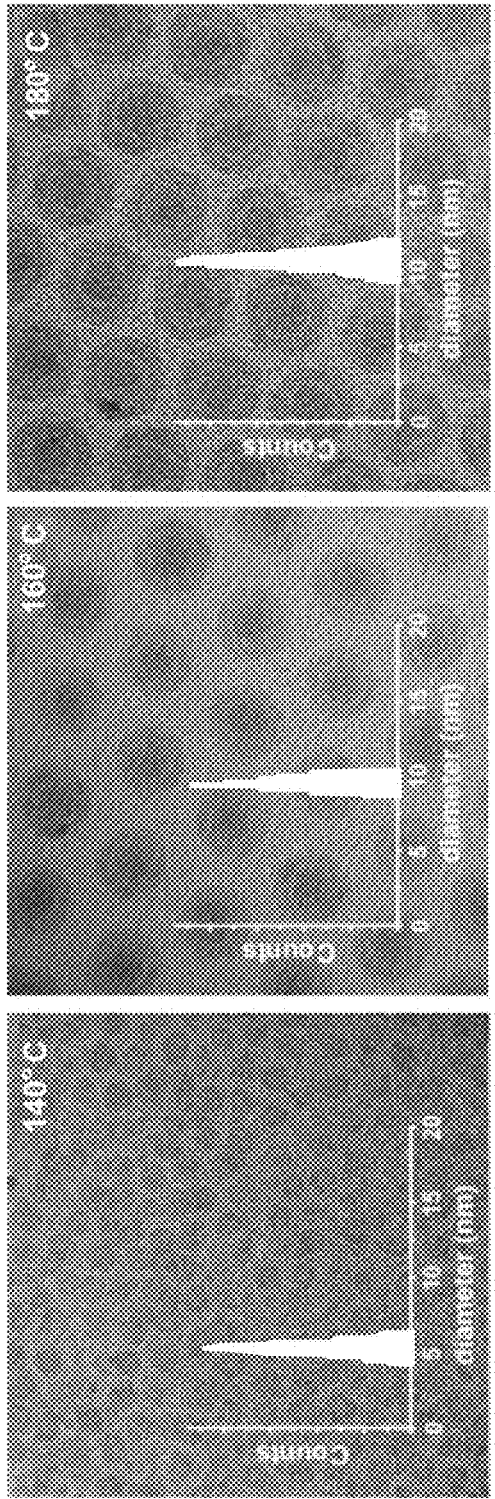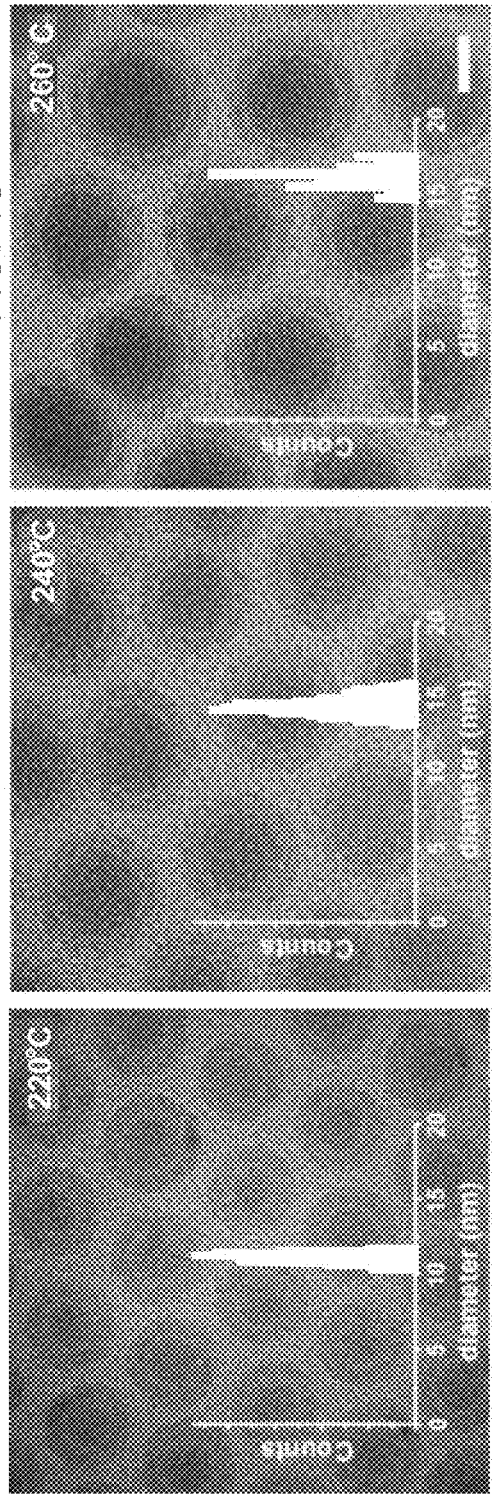
FIG. 4A  FIG. 4B  FIG. 4C
FIG. 4D  FIG. 4E  FIG. 4F

MAGNETIC NANOPARTICLES

CROSS-REFERENCE TO RELATED APPLICATIONS

This application is a divisional of U.S. application Ser. No. 13/699,378, filed on Nov. 21, 2012, which is a 371 of International Application No. PCT/US2011/038143, filed May 26, 2011, which claims the benefit of priority from U.S. Provisional Application Ser. No. 61/348,561, filed on May 26, 2010, each of which is incorporated herein by reference in its entirety.

FEDERALLY SPONSORED RESEARCH OR DEVELOPMENT

This invention was made with Government support under Grant No. UO1 HL080731-02 awarded by the National Institutes of Health. The Government has certain rights in the invention.

FIELD OF THE INVENTION

The present disclosure relates to magnetic nanoparticles.

BACKGROUND

Magnetic nanoparticles that are biocompatible and/or degradable can have broad applications in biotechnology and medicine. In particular, given that biological samples and tissues have intrinsically low magnetic susceptibility, magnetic nanoparticles can offer an efficient contrast mechanism for highly selective detection. For example, magnetic nanoparticles can be used in applications including, but not limited to, bio-separation, drug delivery, and gene transfer.

SUMMARY

The present disclosure relates to magnetic nanoparticles and methods for their synthesis and use. Each magnetic nanoparticle includes a magnetic core and a biocompatible outer shell, in which the outer shell both protects the core from oxidation and enhances magnetic properties of the nanoparticle. The enhanced magnetic properties can include increased magnetization and reduced coercivity of the magnetic core, allowing for highly sensitive detection as well as diminished non-specific aggregation of nanoparticles. By forming biocompatible nanoparticles having enhanced magnetic properties, detection of specific target molecules, e.g., proteins and single cells, can be improved.

In general, one aspect of the subject matter described in this specification can be embodied in a nanoparticle that includes a ferromagnetic core and a superparamagnetic shell surrounding the magnetic core.

In some implementations, the nanoparticle has a diameter greater than or equal to about 2 nm. In some cases, the ferromagnetic inner core has a core diameter in the range of about 1 nm to about 15 nm. In some instances, the super-paramagnetic shell has a thickness greater than or equal to about 0.1 nm. The ferromagnetic core can include Fe, Co, Ni, FePt or SmCo.

In some implementations, the superparamagnetic shell includes an oxide of a magnetic material. In some cases, the super-paramagnetic shell includes a dopant material. The dopant can include a metal selected from the group consisting of Mn, Co, Ni, Zn, and ZnMn.

In some instances, the nanoparticle includes a coating on the super-paramagnetic shell, in which the coating is configured to increase the aqueous solubility of the nanoparticle. The coating can include 2,3-dimercaptosuccinic acid (DMSA).

In some cases, the nanoparticle includes a coating on the super-paramagnetic shell, in which the coating is configured to bind the nanoparticle to a target molecule.

In some implementations, the nanoparticle includes a dextran polymer coating on the superparamagnetic shell.

In certain implementations, the superparamagnetic shell includes iron oxide.

In another aspect, a method of forming a nanoparticle, the method includes forming one or more ferromagnetic nanoparticle cores; and forming a super-paramagnetic shell on each of the one or more ferromagnetic nanoparticle cores. Forming the ferromagnetic nanoparticle can include combining a metal complex and a surfactant in a first solution and annealing the first solution to thermally decompose the metal complex and to form the one or more ferromagnetic nanoparticle cores in the first solution.

In some implementations, forming the super-paramagnetic shell on the one or more ferromagnetic nanoparticle cores includes, subsequent to annealing the first solution, combining one or more metal-oleate complexes to the first solution to form a second solution, and annealing the second solution to form the super-paramagnetic shell on the one or more ferromagnetic nanoparticle shells.

In another aspect, a method of determining the presence of a target molecule in a subject includes administering to the subject a nanoparticle, in which the nanoparticle includes a ferromagnetic core, a super-paramagnetic shell, and a targeting moiety on the super-paramagnetic shell that specifically binds to the target molecules, providing sufficient time for the nanoparticle to bind to the target molecule, and generating a magnetic resonance image of the subject, wherein a signal in the image indicates the presence of the target molecule.

In another aspect, a method of treatment includes administering to the subject a nanoparticle, in which the nanoparticle includes a ferromagnetic core, a super-paramagnetic shell, and a coating on the super-paramagnetic shell to bind to a target cell of the subject, providing sufficient time for the nanoparticle to bind to the target cell, and applying an alternating electro-magnetic field to the subject to treat the target cell.

A crosslinked polymer is a polymer in which functional groups on a polymer chain and/or branches have reacted with functional groups on another polymer to form polymer networks.

A non-crosslinked polymer is a polymer in which few or no individual polymer chains have reacted with the functional groups of another polymer chain to form an interconnected polymer network.

Magnetic moment is the tendency of a magnet to align with a magnetic field.

Magnetic coercivity is the resistance of a ferromagnetic material to becoming demagnetized.

Magnetic susceptibility is the degree of magnetization of a material in response to an applied magnetic field.

Superparamagnetism refers to materials that do not exhibit magnetic properties when no magnetic field is applied, but behave similar to a magnet upon the application of a magnetic field.

The invention provides several advantages. For example, in some implementations, the outer shell of the magnetic nanoparticle prevents progressive oxidation of the nanoparticle core, which, in turn, prevents a reduction in the overall magnetization of the nanoparticle. In some cases, doping the outer shell of the magnetic nanoparticle with metals can improve the overall magnetization of the nanoparticle. The magnetic nanoparticle has the advantage of a stable outer shell, in that the shell's thickness is generally constant over time. In certain implementations, the outer shell of the magnetic nanoparticle provides a biocompatible surface onto which a target molecule or other binding moiety can be attached. Due to the high magnetization of the magnetic nanoparticles, they can be useful for highly sensitive detection of such target molecules and/or moieties. Furthermore, due to the superparamagnetic shell, the magnetic nanoparticle core exhibits little or no coercivity at low magnetic fields. Accordingly, non-specific aggregation of multiple magnetic nanoparticles can be avoided in the absence of an externally applied magnetic field. Conversely, intentional aggregation of the magnetic nanoparticles can be induced when an external magnetic field above a set threshold is applied. Such induced aggregation can be useful for collection and/or isolation of particular target molecules attached to the magnetic nanoparticles.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages will be apparent from the following detailed description, the figures and from the claims.

BRIEF DESCRIPTION OF DRAWINGS

FIGS. 3A to 3D are images of nanoparticle cores fabricated from metal complex:surfactant solutions, each containing a different molar ratio of the metal complex to surfactant.

FIGS. 4A to 4F are images of nanoparticle cores fabricated from metal complex:surfactant solutions at different reaction temperatures.

DETAILED DESCRIPTION

Preferably, a magnetic nanoparticle has a high magnetic moment to enhance the selectivity of the nanoparticle for detection. Although increasing the nanoparticle size can lead to a higher magnetic moment, a nanoparticle that is too large can be difficult to use to detect small molecules and cells. Additionally, in some instances, magnetic particles are susceptible to oxidation, which can reduce magnetization over time. Also, due to the magnetic nature of particles, spontaneous aggregation can occur, which can make nanoparticles difficult to use in applications and which can make selective binding of molecules to nanoparticles difficult.

The present disclosure relates to magnetic nanoparticles and methods for their synthesis and use. Each magnetic nanoparticle includes a magnetic core and a biocompatible outer shell, in which the outer shell both protects the core from oxidation and enhances magnetic properties of the nanoparticle. The enhanced magnetic properties can include increased magnetization and reduced coercivity of the magnetic core, allowing for highly sensitive detection as well as diminished non-specific aggregation of nanoparticles. By forming biocompatible nanoparticles having enhanced magnetic properties, detection of specific target molecules, e.g., proteins and single cells, can be improved.

Magnetic Nanoparticles

Figure 1A:
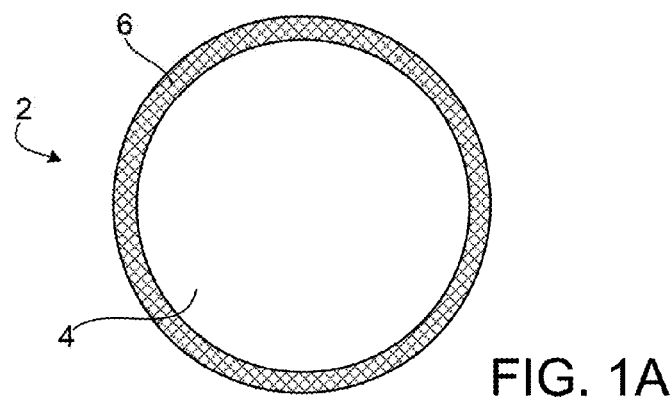
FIGS. 1A and 1B are cross-sections of exemplary magnetic nanoparticles.

FIG. 1A shows a cross-section of an exemplary magnetic nanoparticle 2. The magnetic nanoparticle 2 includes a nanoparticle core 4 that is surrounded by an outer shell 6. Although shown as having a circular cross-section (a sphere in 3 dimensions), the magnetic nanoparticle 2 can have various shapes. For example, the magnetic nanoparticle 2 can be shaped similar to a rod/cylinder, a wire, or a whisker. The nanoparticle can have other shapes as well. The magnetic nanoparticle 2 also can have various sizes. In some cases, the magnetic nanoparticle can have an average maximum dimension that ranges anywhere between about 1 nm to about 20 nm, including, for example, about 2 nm, about 5 nm, about 10 nm, about 15 nm, or about 16 nm.

In some implementations, the nanoparticle core 4 is formed from ferromagnetic materials that are crystalline, poly-crystalline, or amorphous in structure. For example, the nanoparticle core 4 can include materials such as, but not limited to, Fe, Co, Ni, FeOFe$_2$O$_3$, NiOFe$_2$O$_3$, CuOFe$_2$O$_3$, MgOFe$_2$O$_3$, MnBi, MnSb, MnOFe$_2$O$_3$, Y3Fe$_5$O$_{12}$, CrO$_2$, MnAs, SmCo, FePt, or combinations thereof. The nanoparticle core 4 can have a shape similar to the entire magnetic nanoparticle 2. For example, the nanoparticle core 4 can be shaped similar to a sphere, a rod/cylinder, a wire or a whisker. The nanoparticle core 4 can have other shapes as well. The average maximum dimension of the nanoparticle core 4 can vary from about 1 nm to about 20 nm including, for example, about 2 nm, about 5 nm, about 10 nm, or about 15 nm.

The outer shell 6 of the magnetic nanoparticle 2 partially or entirely surrounds the nanoparticle core 4. In some implementations, the shell 6 is formed from a superparamagnetic material that is crystalline, poly-crystalline, or amorphous in structure. In some cases, the material used to form the shell is biocompatible, i.e., the shell material elicits little or no adverse biological/immune response in a given organism and/or is non-toxic to cells and organs. Exemplary materials that can be used for the shell 6 include, but are not limited to, metal oxides, e.g., ferrite ($Fe_3O_4$), FeO, Fe2O3, $CoFe_2O_4$, $MnFe_2O_4$, $NiFe_2O_4$, $ZnMnFe_2O_4$, or combinations thereof. The shell 6 can have a thickness that ranges from about 0.5 nm to about 3 nm, including, for example, about 1 nm, about 1.5 nm, about 2 nm, or about 2.5 nm.

The outer shell 6 of the magnetic nanoparticle 2 can serve various functions. For example, when an isolated nanoparticle core without a shell is exposed to an oxidizer (such as oxygen in the air), all or a portion of the core material can oxidize leading to degradation in the magnetic properties of the nanoparticle. In addition, the oxide that is formed can have weak magnetic properties relative to the core material. Forming the outer shell 6 over the core 4, however, can prevent undesirable oxidation of the core material and thus preserve the magnetic properties of the core 4. Additionally, in some implementations, the shell 6 enhances the magnetic properties of the nanoparticle core 4. For example, a magnetic nanoparticle with the shell 6 can exhibit a magnetic moment that is about 10 times, about 100 times, or about 1000 times greater than a magnetic moment of a nanoparticle core formed from the shell material alone.

The magnetization (magnetic moments per unit volume of particles) of the magnetic nanoparticle 2 depends, in part, on the maximum average dimension of the core 4, the thickness of the shell 6, as well as the magnetization of the core 4 and shell 6, respectively. For example, the overall magnetization ($M_0$) of $Fe@Fe_3O_4$ particles consists of individual contributions from the Fe core and the ferrite shell, given as given as the volume-weighted average, $$M_0 = \frac{V_{Fe}}{V_{Fe} + V_{Ferrite}} \cdot M_{Fe} + \frac{V_{Fe}}{V_{Fe} + V_{Ferrite}} \cdot M_{Ferrite},$$

where $M_{Fe}$ and $M_{Ferrite}$ are the magnetization and $V_{Fe}$ and $V_{Ferrite}$ are the volumes of the core and the shell, respectively.

In some cases, the shell material corresponds to an oxide of the core material, in which the oxide is coated over a surface of the nanoparticle core 4 in a controlled process, without further oxidizing the core 4, rather than being formed from the core material itself. This controlled shell formation process can produce a shell having a stable thickness over time (i.e., there is little or no increase in the shell thickness) and which has strong magnetic properties. In addition, by forming the shell 6 over a surface of the nanoparticle core 4, there is no reduction in the size of the nanoparticle core.

Due to the superparamagnetic properties of the shell 6, the magnetic nanoparticle 2 exhibits little or no magnetic properties when no external magnetic field is applied to the nanoparticle 2. In contrast, when an external magnetic field is applied to the nanoparticle 2 above a set threshold, the nanoparticle exhibits the enhanced magnetic moment described above. That is to say, the shell 6 alters the magnetic properties of the nanoparticle 2 such that the entire nanoparticle 2 appears to be superparamagnetic. The threshold for exhibiting the enhanced magnetic moment is based on the material and structure of the shell 6.

The reduction and/or lack of a magnetic moment in the absence of an externally applied magnetic field can, in some implementations, reduce and/or prevent non-specific/spontaneous aggregation of groups of the nanoparticles 2 that can otherwise occur due to their magnetic properties. In contrast, by applying an external magnetic field to multiple nanoparticles having the core/shell structure described above, it is possible, in some implementations, to induce aggregation of the nanoparticles. Such induced aggregation can be useful when attempting to detect analytes or other molecules bound to the magnetic nanoparticles.

In some implementations, the magnetic moment of the nanoparticle 2 can be enhanced even further by including a dopant in the shell material. For example, the shell 6 can be doped with metals including, but not limited to, Mn, Co, Ni, Zn, ZnMn, and combinations thereof. The presence of dopants in the nanoparticle shell 6 also can affect the point at which the nanoparticle 2 exhibits magnetic properties when in the presence of an externally applied magnetic field. Magnetic nanoparticle can have the highest magnetic moment when the dopant ion should be composed level to half of Fe, for example, MnFe2O4, CoFe2O4, NiFe2O4, ZnFe2O4, ZnMnFe2O4.

Figure 1B:
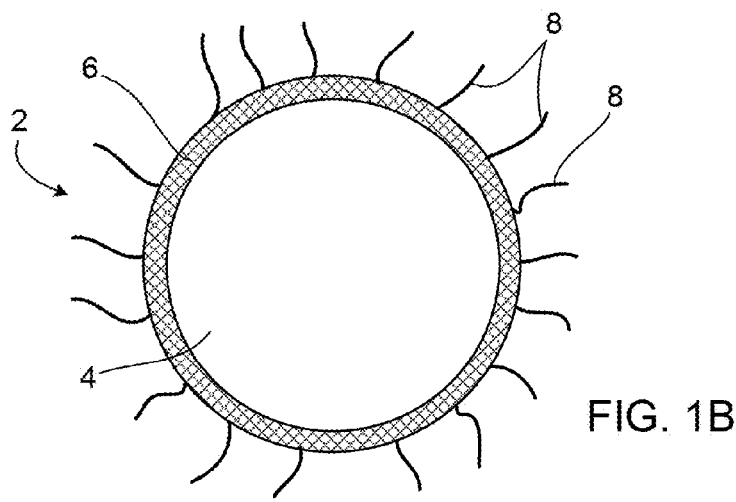

In some implementations, the magnetic nanoparticle 2 also includes a surface coating. For example, FIG. 1B shows a nanoparticle 2 in which a surface coating 8 is formed on a surface of the superparamagnetic shell 6. The surface coating 8 entirely or partially covers the shell 6. At least one purpose of the coating 8 is to provide a biocompatible surface that can be easily functionalized with targeting moieties, binding groups, and the like. In some cases, the surface coating 8 makes the magnetic nanoparticle essentially hydrophilic or hydrophobic. The surface coating 8 can be formed of polymers including, but not limited to, synthetic polymers such as polyethylene glycol or silane, natural polymers, derivatives of either synthetic or natural polymers, and combinations thereof. A natural polymer is obtained when a pure polymer, such as a polysaccharide, is synthesized by a microorganism, plant, or animal and extracted in substantially pure form. A synthetic polymer is obtained from nonbiological syntheses, by using standard polymer chemistry techniques known to those in the art to combine monomers into polymers. The polymers can be homopolymers, i.e., synthesized from a single type of monomer, or co-polymers, i.e., synthesized from two or more types of monomers. The polymers can be crosslinked or non-crosslinked Crosslinked polymers are characterized as being heat stable and resistant to breakdown in biological systems. A crosslinked polymer has a molecular weight significantly higher than the original starting polymer.

In some implementations, the surface coating 8 is not a continuous film around the magnetic nanoparticle 2, but is a "mesh" or "cloud" of extended polymer chains attached to and surrounding the magnetic nanoparticle 2. Exemplary polymers include, but are not limited to polysaccharides and derivatives, such as dextran, pullanan, carboxydextran, carboxymethyl dextran, and/or reduced carboxymethyl dextran, polymethylmethacrylate polymers and polyvinyl alcohol polymers. In some implementations, these polymer coatings provide a surface to which targeting moieties and/or binding groups can bind much easier than to the shell material.

For example, dextran-coated nanoparticles can be made and cross-linked with epichlorohydrin. The addition of ammonia reacts with epoxy groups to generate amine groups. This material is known as cross-linked iron oxide or "CLIO" and when functionalized with amine is referred to as amine-CLIO or $NH_2$-CLIO. Carboxy-functionalized nanoparticles can be converted to amino-functionalized magnetic particles by the use of water-soluble carbodiimides and diamines such as ethylene diamine or hexane diamine.

Avidin or streptavidin can be attached to nanoparticles for use with a biotinylated binding moiety, such as an oligonucleotide or polypeptide. Similarly, biotin can be attached to a nanoparticle for use with an avidin-labeled binding moiety.

In other implementations, the nanoparticles are associated with non-polymeric functional group compositions. Methods are known to synthesize stabilized, functionalized nanoparticles without associated polymers, which are also within the scope of this invention. Such methods are described, for example, in Halbreich et al., Biochimie, 80 (5-6):379-90, 1998 and Caroline R. A. Valois et al., Biomaterials, 31(2): 366-374.

In general, a binding moiety is a molecule, synthetic or natural, that specifically binds or otherwise links to, e.g., covalently or non-covalently binds to or hybridizes with, a target molecule, or with another binding moiety (or, in certain embodiments, with an aggregation inducing molecule). For example, the binding moiety can be a synthetic oligonucleotide that hybridizes to a specific complementary nucleic acid target. The binding moiety can also be an antibody directed toward an antigen or any protein-protein interaction. Also, the binding moiety can be a polysaccharide that binds to a corresponding target. In certain embodiments, the binding moieties can be designed or selected to serve, when bound to another binding moiety, as substrates for a target molecule such as enzyme in solution. Binding moieties include, for example, oligonucleotide binding moieties, polypeptide binding moieties, antibody binding moieties, and polysaccharide binding moieties.

Synthesis of Magnetic Nanoparticles

Figure 2:
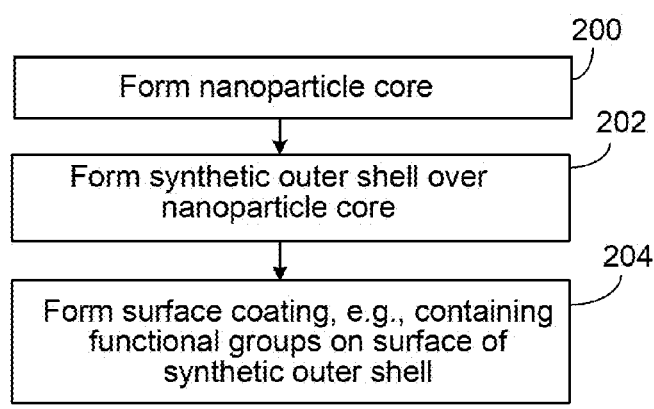
FIG. 2 is a flow chart depicting an exemplary process for fabricating a magnetic nanoparticle.

FIG. 2 shows a flow chart depicting an exemplary process for fabricating a magnetic nanoparticle. As shown in FIG. 2, fabrication of the magnetic nanoparticle can begin by forming the nanoparticle core (step 200). To fabricate the nanoparticle core, metal complexes are thermally decomposed in a solution containing a surfactant. In some cases, the thermal decomposition occurs in an oxygen-free environment (e.g., under vacuum or nitrogen environment) to avoid oxidation of the nanoparticle cores that are formed in the reaction. In an example, a solution of 1-octadecene (ODE) and oleylamine (OY) surfactant is heated to a temperature of 250° C. When the temperature of the solution is stabilized, a metal complex, such as $Fe(CO)_5$, is added to solution and stirred. Fe magnetic nanoparticle (Fe MNP) cores form and precipitate out of the solution. The solution then is cooled to room temperature. Examples of other metal complexes include, but are not limited to, $Fe(acac)_2$ (where acac is acetylacetonate), $Fe(acac)_3$, cobalt complexes, nickel complexes, and. Examples of other surfactants include, but are not limited to, oleyamine, oleic acid and other chemicals containing amine or carboxylic acid chemical functional groups.

The nanoparticle core size depends, in part, on the molar ratio of metal source and surfactant. In some implementations, decreasing levels of surfactant relative to the metal source can result in increasing particle size. For example, FIG. 3 shows images of Fe nanoparticle cores fabricated from a solution containing OY and an iron metal complex, in which the molar ratio ([Fe]:[OY]) was varied at a fixed temperature from 5:1 to 35:1. When the ratio changed from 5:1 to 12:1, the growth of the particle diameter was only about 2 nm. Once the ratio exceeded 12:1, the particle size stabilized at about 2 nm.

The nanoparticle core size also can depend on the temperature of the reaction during which the nanoparticle cores are formed. In some implementations, raising a temperature at which the reaction takes place leads to increasing particle size. For example, FIGS. 4A to 4F show images of Fe nanoparticle cores fabricated from a solution containing OY and an iron metal complex, in which the temperature of the reaction during which the nanoparticle cores were formed was varied from 140° C. to 260° C. at a fixed molar ratio ([Fe]:[OY]). As the reaction temperature was raised stepwise from 140° C. to 260° C., the nanoparticle core diameter increased from about 4.4 nm to about 14.5 nm.

Figure 4G:
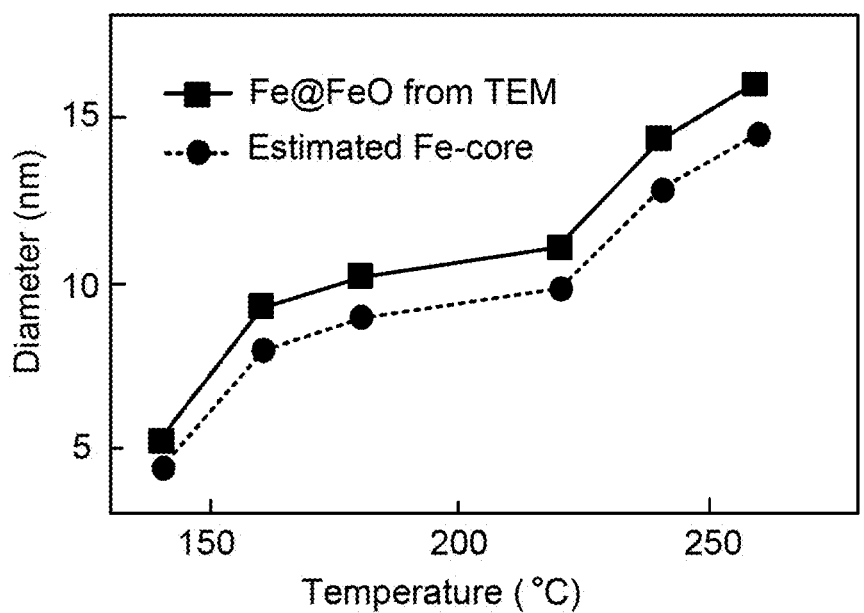
FIG. 4G is a graph that shows nanoparticle diameter versus reaction temperature.

In each of the images of the exemplary nanoparticle cores shown in FIGS. 3 and 4, a natural amorphous ferrite shell (FeO) that is formed from exposure to air and subsequent oxidation of the nanoparticle core material is visible. The natural amorphous shell has weak or no magnetic properties and can gradually thicken over time so as to transform the Fe core into the amorphous oxide. The foregoing diameters of the exemplary nanoparticles were estimated by adjusting for the volume of the ferrite shell. FIG. 4G is a graph that shows the nanoparticle core diameter with the naturally occurring oxide shell and the estimated nanoparticle core diameter without the naturally occurring oxide shell versus reaction temperature.

Referring again to FIG. 2, following fabrication of the nanoparticle core, a synthetic shell is formed (step 202) on a surface of the core particle. To fabricate the shell, a separate solution containing metal complexes can be prepared and then added to the solution containing the magnetic nanoparticle cores. To prevent the natural amorphous ferrite shell from forming prior to fabricating the synthetic shell, the solution containing the nanoparticle cores can be maintained in an oxygen-free environment (e.g., under vacuum or primarily nitrogen environment). The combined mixture then can be annealed to form the nanoparticle shell on a surface of the nanoparticle core.

In an example, a solution of iron-oleate complex is separately prepared from the foregoing solution containing the Fe MNP cores. In particular, a solution containing $Fe(CO)_5$, oleic acid (OA), and ODE is prepared and annealed, preferably under an air-free environment. After cooling, the new solution then is transferred to a solution containing the Fe MNP cores. The temperature of the mixture containing the Fe MNP cores and metal complexes then is increased to form a synthetic shell around the Fe MNP cores. In particular, the reactor temperature is slowly heated to an optimal annealing temperature (e.g., 300° C.) to form Fe MNPs having a Fe core and a synthetic polycrystalline ferrite shell ($Fe_3O_4$), in which the synthetic shell exhibits superparamagnetic properties. The synthetic shell serves as barrier which prevents oxidation of the core and is generally stable, exhibiting no change in thickness over time. After cooling the mixture, the magnetic nanoparticles having superparamagnetic shells can be collected, e.g., via centrifugation.

In some implementations, the process of forming the synthetic outer shell of the magnetic nanoparticle can include adding additional different metal complexes to the solution containing the MNP cores. The additional different metal complexes can contribute one or more dopants to the synthetic outer shell of a subsequently formed magnetic nanoparticle, in which the dopants can enhance the magnetic properties (e.g., magnetic moment) of the MNPs. One or more combinations of different metal complexes (e.g., $Ni(CO)_4$, $Co_2(CO)_8$) can be added to the solution to form one or more dopants in the synthetic shell. In an example, $Mn_2(CO)_{10}$ is added to the foregoing mixture containing the Fe MNP cores and the Fe metal complexes, prior to heating to the mixture. As before, the reactor temperature is slowly heated to an optimal annealing temperature (e.g., 300° C.) to form Fe MNPs having a Fe core and a synthetic polycrystalline ferrite shell ($Fe_2O_4$) doped with Mn ($Fe@MnFe_2O_4$).

In some implementations, the MNPs can be further processed to form a surface coating (step 204) on the synthetic shell, in which the surface coating includes functional groups to link the MNP to a binding moiety. As previously explained, the surface coating can include a functionalized polymeric or non-polymeric coating. In some cases, the coating can increase or decrease the wetting properties of the MNP. The polymeric or non-polymeric coating can provide an exposed functional group for binding to a specific or non-specific moiety. For example, the functional group can include an amino, carboxyl, or other reactive group for binding to a specific or non-specific moiety. In some implementations, the moiety can include oligonucleotides that have terminal amino, sulfhydryl, or phosphate groups, among others, that bind to amino or carboxy groups. Alternatively, a binding moiety can be attached to magnetic nanoparticles via a functionalized polymer that is formed on the synthetic MNP shell. Various non-limiting examples of methods for synthesizing functionalized, coated nanoparticles are described below.

In an example, a non-polymeric coating of DMSA can be formed on a surface of the synthetic shell (see, e.g., Albrecht et al., Biochimie, 80 (5-6): 379-90, 1998). DMSA is coupled to the synthetic ferrite shell, providing an exposed functional group. In another example, carboxy functionalized surface coatings can be synthesized on a MNP according to the method of Gorman (see WO 00/61191). In this method, reduced carboxymethyl (CM) dextran is synthesized from commercial dextran. The CM-dextran and iron salts are mixed together and are then neutralized with ammonium hydroxide. The resulting carboxy functionalized nanoparticles can be used for coupling amino functionalized oligonucleotides.

In another example, carboxy-functionalized MNPs can also be made from polysaccharide coated MNPs by reaction with bromo or chloroacetic acid in a strong base to attach the carboxyl groups. In addition, carboxy-functionalized particles can be made from amino-functionalized MNPs by converting the amino groups to carboxy groups using reagents such as succinic anhydride or maleic anhydride.

In another example, dextran-coated MNPs can be made and cross-linked with epichlorohydrin. The addition of ammonia will react with epoxy groups to generate amine groups (see, e.g., U.S. Patent App. Pub. No. 20030124194 and U.S. Patent App. Pub. 20030092029, incorporated herein by reference, Hogemann, D., et al., "Improvement of MRI probes to allow efficient detection of gene expression," Bioconjug. Chem. 2000. 11(6):941-6, and Josephson et al., "High-efficiency intracellular magnetic labeling with novel superparamagnetic-Tat peptide conjugates," Bioconjug. Chem., 1999, 10(2):186-91). This material is known as cross-linked iron oxide or "CLIO" and when functionalized with amine is referred to as amine-CLIO or $NH_2$-CLIO.

In another example, carboxy-functionalized MNPs can be converted to amino-functionalized magnetic particles by the use of water-soluble carbodiimides and diamines such as ethylene diamine or hexane diamine. In some implementations, avidin or streptavidin can be attached to nanoparticles for use with a biotinylated binding moiety, such as an oligonucleotide or polypeptide (see, e.g., Shen et al., "Magnetically labeled secretin retains receptor affinity to pancreas acinar cells," Bioconjug. Chem., 1996, 7(3):311-6). Similarly, biotin can be attached to a nanoparticle for use with an avidin-labeled binding moiety.

Characterization of MNPs

The properties of the MNPs can be characterized using various techniques. For example, the magnetic properties of the MNPs can be evaluated by examining zero-field-cooled and field-cooled magnetization curves. In an example, $Fe@MnFe_2O_4$ MNPs were fabricated and evaluated using an extended Stoner-Wohlfarth magnetization model. The model was developed to explain the magnetic behavior for an ensemble of identical, single domain nanoparticles that are randomly oriented and noninteracting with one another. We have further extended this model to reflect the real physical system with $Fe@MFe_2O_4$ particles as summarized below.

To accommodate the cubic magnetocrystalline anisotropy nature of Fe and ferrite, we adopted the framework developed by Joffe and Heuberger.

The influence of thermal activation on magnetization was included by allowing the thermally-activated reversal of magnetic moments.

We used the size distribution functions obtained by TEM analysis to account for the size variation in an ensemble of particles.

Using the method, in which it was determined that the synthetic shell followed a typical superparamagnetic curve whereas the nanoparticle core assumed a stable single-domain behavior with non-zero coercivity ($H_c$=350 Oe). The total magnetization of the MNP (i.e., the volume-weighted average of the magnetization of the core and shell), however, had considerably reduced coercivity ($H_c$=40 Oe) compared to the coercivity of the nanoparticle core. In the example, the superparamagnetic contribution from the synthetic shell saturates to overwhelm the relatively slow magnetization of the nanoparticle core at low magnetic fields. In contrast, the contribution of the core towards magnetization becomes dominant at higher magnetic fields to increase the overall magnetization of the MNP. Other techniques, such as micromagnetic simulation and measurements of nuclear magnetic relaxation dispersion, can be used to further characterize the MNPs.

Uses of MNPs

Magnetic nanoparticles can be used in various applications, including in medicine as biologically compatible and environmentally sensitive sensors and/or molecular imaging agents. For example, the MNPs can be used as magnetic resonance-based sensors in which the MNPs are used as remote sensors for detecting various analytes in an aqueous, (i.e., water-containing) sample and can be used for the continuous monitoring of changing levels of analytes in the aqueous sample. The MNPs can be suspended or suspendable in an aqueous liquid phase and be covalently or non covalently linked to, or otherwise have immobilized thereon, one or more moieties selected to alter the state of aggregation of the MNPs as a function of the presence or concentration of the analyte in the solution (see, e.g., U.S. Patent App. Pub. No. 20060269965, incorporated herein by reference).

In another example, the MNPs can be used in aggregate formation assays to detect target molecules (see, e.g., U.S. Patent App. Pub. No. 20030092029, incorporated herein by reference). In the aggregate formation assays, a population of conjugates (or a mixture of two or more populations of conjugates with differing binding moieties directed to a target molecule or type of target molecule) is placed into a sample solution. Each conjugate comprises one or more binding moieties (e.g., an oligonucleotide, nucleic acid, polypeptide, or polysaccharide) linked, e.g., covalently or non-covalently, to a magnetic, e.g., superparamagnetic, nanoparticle. The binding moiety causes a specific interaction with a target molecule (or, in some embodiments, an aggregation inducing molecule, such as avidin). The binding moiety specifically binds to a selected target molecule, which can be, for example, a nucleic acid, polypeptide, or polysaccharide. As a result, the dispersed state of the conjugates switches to an aggregated state, which decreases a spin-spin relaxation time (T2) of adjacent water protons in the aqueous solution. In some cases, the MNPs can be used for magnetic separation of target molecules, e.g., protein.

In another example, the MNPs can be used to detect target molecules in aggregate dispersion assays (see, e.g., U.S. Patent App. Pub. No. 20030092029, incorporated herein by reference). In aggregate dispersion assays, conjugates are used to prepare small aggregates, and the aggregates are placed into a sample solution. In this assay system, the binding moieties are designed so that they can be bound to each other (or to a specific aggregation inducing molecule, such as avidin) to form the aggregates, and to be (or form upon binding to each other or to the aggregation inducing molecule) a substrate that is cleaved by a specific target molecule. If the sample solution contains a target molecule, the substrate formed by the binding moieties is cleaved, resulting in the dissolution of the aggregates. Thus, the aggregated state switches to a dispersed state, which increases T2 relaxation times.

The aggregates in these assay systems can be observed and detected in vitro, e.g., in vials or arrays, e.g., 2-D or 3-D arrays, as well as in vivo, e.g., using MR imaging of a subject after administration of the conjugates or aggregates. In some cases, the MNPs can be used for imaging without requiring aggregation of multiple nanoparticles. Further explanation of the foregoing uses can be found in, e.g., U.S. Pat. Nos. 6,818,199, 6,203,778, and 5,766,572, Jae-Hyun Lee et al., Nature Medicine 13:95-99; Daniel L. J. Thorek Annals of Biomedical Engineering 2006, 23-38.

In another example, the MNPs can be bound to target cells, such as cancer cells, for use in magnetic hyperthermia. In particular, conjugated MNPs can be provided to a cancerous cell or tissue, either in vitro or in vivo, in which the conjugated MNPs bind to the cancerous cell/tissue. In some implementations, the MNPs include targeting moieties that cause the MNPs to bind to specific cancer cells and/or cause the MNPs to travel to specific parts of a subject's body when injected systemically. See, e.g., Maite Lewin et al., Nature Biotechnology 18:410-414; PCT No. PCT/KR07/00961. Subsequently, an externally applied alternating magnetic field (e.g., 100 kHz) is applied to the bound MNPs such that the motion of the MNPs in response to the applied field generates an increase in thermal energy to treat the target cells/tissue. In particular, the increase in thermal energy can lead to destruction of the cancerous cells/tissue.

In another example, the MNPs can be used in magnetofection. In magnetofection, conjugated MNPs are bound to a target molecule, such as nucleic acid, and a magnetic field then is applied to the molecule bound MNPs to deliberately introduce and concentrate the particles into one or more target cells. The nucleic acids can then be released into the cell cytoplasm by various different mechanisms such as, for example: 1) the proton sponge effect, which is caused by cationic polymers coated on the MNPs that promote endosome osmotic swelling, disruption of the endosome membrane and intracellular release of the nucleic acid; or 2) the destabilization of the endosome by cationic lipids coated on the MNPs that release the nucleic acid into the cell by flip-flop of cell negative lipids and charge neutralization. See, e.g., U.S. Pat. No. 7,635,734 and Eric M Pridgen et al., Nanomedicine 2(5):669-680.

EXAMPLES

The invention is further described in the following examples, which do not limit the scope of the invention described in the claims.

Example 1

Synthesis and Characterization of Ferromagnetic Iron Core/Superparamagnetic Iron Oxide Shell Nanoparticles We initially prepared Fe MNP cores. 20 mL ODE and 0.3 mL OY (0.64 mmol) were added into a 250 mL 3-neck glass round-bottom flask. A condenser and a thermocouple were connected to separate necks of the flask. The mixture was heated up to 60° C. under vacuum for 1 hour and recharged with $N_2$ gas to completely remove $O_2$. This procedure was repeated twice. The mixture was then heated to the desired temperature (e.g., 260° C. for 16-nm Fe MNP cores). When the temperature became stable, $Fe(CO)_5$ (1.4 mL, 10 mmol) was carefully injected into the reactor whilst vigorously stirring; the solution quickly turned black as the carbonyl decomposed and nanoparticles began forming. The solution was kept at this elevated temperature and under $N_2$ flow for 1 hour, after which it was cooled to room temperature.

While the Fe-only MNP cores were formed, a manganese and iron-oleate complex was separately prepared. $Mn_2(CO)_{10}$ (156 mg, 0.8 mmol), OA (2.3 mL, 7.26 mmol) and 10 mL ODE were added to a 100 mL 3-neck round-bottom flask. The temperature was increased to 60° C. under vacuum for 1 hour and under $N_2$ flow, which was then repeated twice more. The oxygen-free solution was heated to 120° C. and $Fe(CO)_5$ (0.21 mL, 1.61 mmol) was subsequently injected. The mixture was stirred for 30 minutes. The solution turned yellow during this process. No particles, however, were formed due to the relatively low temperature (120° C.). The solution, containing metal-oleate complexes, was cooled to room temperature and then carefully transferred to the Fe-only MNP core solution using double-ended needles. The mixture of Fe-only MNP cores and metal-oleate complexes was stirred for 30 minutes at room temperature. The reactor temperature was then slowly increased at 5° C./minute. We monitored the crystallinity of the nanoparticles during the rise in temperature and determined the optimal annealing temperature (300° C.) for the ferrite-shell formation. When the temperature stabilized, the mixture was stirred for a further hour. Following completion of the reaction, the solution was cooled to room temperature and 150 mL isopropanol solution (ODE/isopropanol=0.2 v/v) was added. The $Fe@MnFe_2O_4$ MNPs were collected via centrifugation (3,000 rpm, 15 minutes) and dispersed in 10 mL hexane. To wash the particles, 50 mL ethanol was added to the particle solution, the mixture was centrifuged, and the precipitate was redispersed in 10 mL hexane. These washing steps were repeated three times to ensure removal of excess chemicals.

Example 2

Magnetic Properties of Core/Shell Nanoparticles

The size of the prepared nanoparticles was characterized using dynamic light scattering (Zetasizer Nano-ZS, Malvern). The shape, structure, and composition were further characterized using a transmission electron microscope (TEM; JEOL 2100, JOEL USA), an X-ray powder diffractometer (XRD; RU300, Rigaku), and an inductively-coupled plasma atomic emission spectrometer (ICP-AES; Activa-S, HORIBA Jobin Yvon), respectively. The magnetic properties were analyzed using a vibrating sample magnetometer (EV-5, ADE Magnetics) and a superconducting quantum interference device (SQUID) magnetometer (MPMS-5, Quantum Design).

Figure 5:
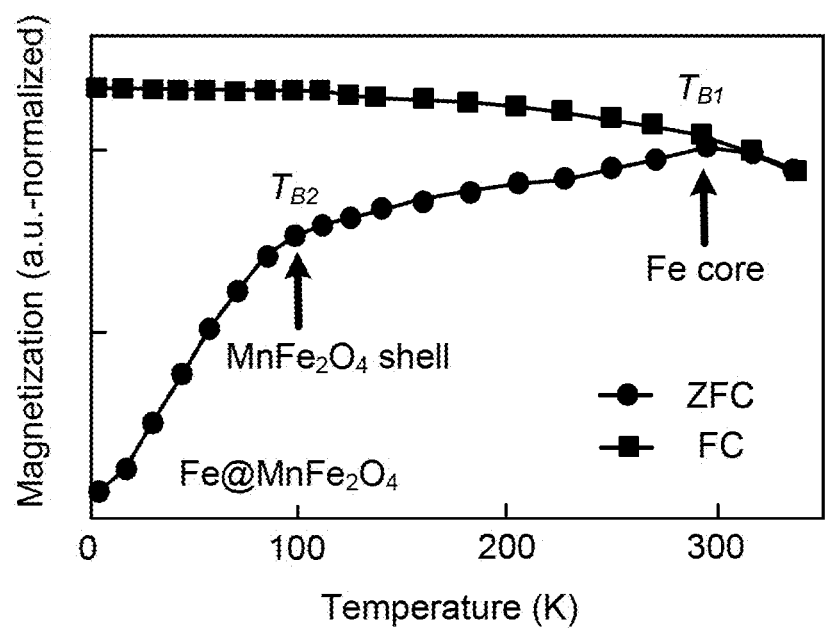
FIG. 5 is a graph that shows normalized magnetization versus temperature for Fe@MFe$_2$O$_4$ (M=Fe, Co, Mn) magnetic nanoparticles (MNPs).

We characterized the magnetic properties of Fe@MFe$_2$O$_4$ MNPs. For comparative analysis, we also synthesized ferrite MNPs with different sizes and compositions. The Ms of all types of Fe-core particles (Fe@FeO and Fe@MFe$_2$O$_4$, M=Fe, Co, Mn) was larger than that of ferrite MNPs with Fe@MnFe$_2$O$_4$ assuming the largest Ms. The ferrite shells had reduced magnetization compared to bulk material, presumably because of their polycrystalline nature. FIG. 5 is a graph that shows zero-field-cooled and field-cooled normalized magnetization for Fe@MFe$_2$O$_4$ (M=Fe, Co, Mn) MNPs, in which peaks are displayed at two different temperatures (TB1>TB2). The two peaks denote the separate onset of superparamagnetism in the Fe core (TB1) and the ferrite shell (TB2). The Fe-core had TB1≈290° C., indicating the stable, ferromagnetic nature of the core at room temperature.

Figure 6A:
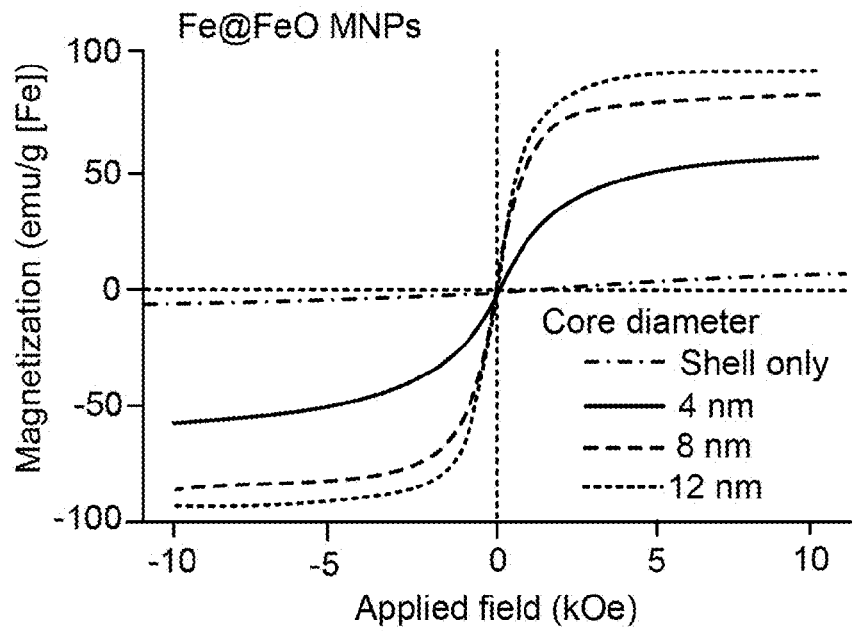
FIGS. 6a-6b are magnetization curves for Fe@FeO MNPs and Fe@MFe$_2$O$_4$ (M=Fe, Co, Mn) magnetic nanoparticles.
Figure 6B:
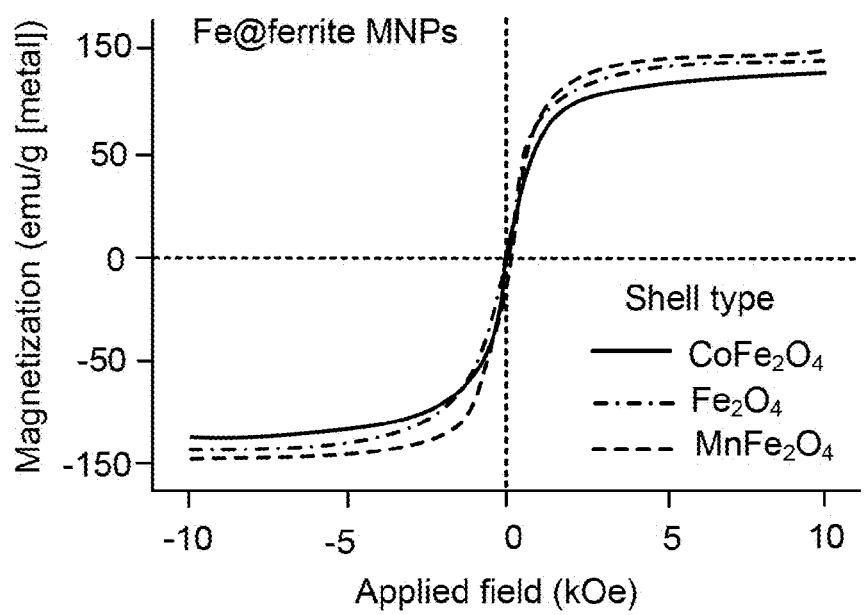

FIGS. 6a-6b are magnetization curves for Fe@FeO MNPs and Fe@MFe2O4 (M=Fe, Co, Mn) MNPs. The magnetization curves were obtained using a vibrating sample magnetometer at T=300 K. All measurements were performed with MNPs in a powder form and 2 hours after synthesis. The number of MNPs in a sample was quantified using an inductively-coupled plasma atomic emission spectroscope (ICPAES). Initially, we analyzed the magnetic properties of Fe@FeO MNPs (FIG. 6a). Hysteresis curves confirmed the superparamagnetic nature of particles with Fe core diameters up to 11 nm. Overall, Ms was observed to increase more in larger particles in parallel to the larger Fe core portions. The Ms of the FeO shell, which was measured using the shell-only MNPs, was relatively small (8 emu/g [Fe]). After compensating for the contribution of the shell, the estimated Ms of the Fe core was 206 emu/g [Fe] (for an 11 nm core), which was close to that of the bulk material (210 emu/g [Fe]).

The magnetization curves of Fe@MFe$_2$O$_4$ (M=Fe, Co, Mn) MNPs each displayed an unusual feature (FIG. 6b) of hysteresis loss concurrent with negligible remanence. In MNPs with the same Fe core size, overall magnetizations followed the same Ms order as that of the shell material (MnFe$_2$O$_4$>Fe$_3$O$_4$>CoFe$_2$O$_4$). This trend thus serves to validate our approach for increasing the overall particle Ms via metal doping of the ferrite shell. Table 1 lists the overall Ms of different types of MNPs, the Ms of the oxide shell, as well as the contribution of the shell towards the overall Ms. As the ferrite only MNPs have no core/shell structure, there is no difference between the overall Ms and the Ms of the iron oxide for those nanoparticles. The Ms for each MNP type was measured at a temperature of 300 K and an external magnetic field strength of H$_{ext}$=10 kOe. The overall diameter of the nanoparticles measured was about 16 nm. The estimated Ms of the ferrite shell is smaller to those of ferrite only MNPs, possibly because of the multi-domain nature of the shell.

TABLE 1

|  | MNP type‡ | Overall M$_s$ of MNPs (emu/g [metal]) | Properties of iron oxide | |
|---|---|---|---|---|
|  |  |  | M$_s$ (emu/g [metal]) | Contribution to Overall M$_s$ (%) |
|  | Fe@FeO | 92 | 8 | 4.9 |
|  | Fe@Fe$_3$O$_4$ | 142 | 58 | 16.4 |
| Fe Core | Fe@CoFe$_2$O$_4$ | 133 | 41 | 12.3 |
|  | Fe@MnFe$_2$O$_4$ | 149 | 69 | 18.8 |
|  | — | — | — | — |
|  | Fe$_3$O$_4$ | 95 | 95 | 100 |
| Ferrite | CoFe$_2$O$_4$ | 92 | 92 | 100 |
|  | MnFe$_2$O$_4$ | 101 | 101 | 100 |

For further analysis, the magnetic properties of Fe@MFe$_2$O$_4$ MNPs were calculated using an extended Stoner-Wohlfarth magnetization model, which includes the effects of non-zero temperature and cubic magnetocrystalline anisotropy. According to the simulated results, the shell (M$_{shell}$) magnetization followed a typical superparamagnetic curve, whereas the core portion (M$_{core}$) assumed stable single-domain behavior with non-zero coercivity (Hc=350 Oe). The total magnetization of a particle (M$_{tot}$), the volume-weighted average of Mcore and Mshell, however, had considerably reduced coercivity (Hc=40 Oe): the superparamagnetic contribution (from the M$_{shell}$) rapidly saturates to overwhelm the relatively slow magnetization of the core at low magnetic fields. The core contribution (M$_{core}$) then becomes dominant at higher magnetic fields to increase the overall M$_{tot}$.

Example 3

Numerical Simulation of Magnetization

Micromagnetic simulation of Fe@MnFe$_2$O$_4$ further corroborated the postulated magnetization mechanism. In the absence of an external magnetic field (H$_{ext}$) and at T=300 K, the magnetization vectors in the Fe-core formed a vortex state, which indicated strong exchange coupling to withstand thermal reversal of the magnetization. In the particle shell, the vectors were randomly oriented, demonstrating a superparamagnetic nature. These configurations qualitatively agreed with zero-field-cooled and field-cooled magnetization measurements, which showed high TB1 for the Fe-core and much lower TB2 for the shell at room temperature. At non-zero field strength, the alignment of magnetic moments was path-dependent and led to the hysteresis loop. A similar simulation with ferrite MNPs showed no hysteresis and the magnetization vectors were randomized by thermal energy at H$_{ext}$=0.

Figure 7:
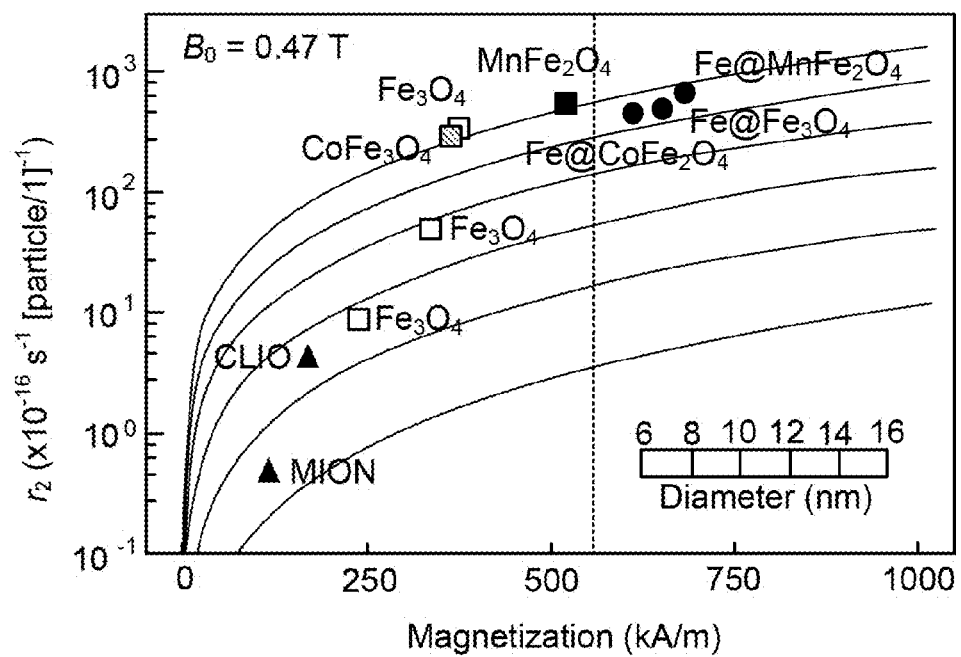
FIG. 7 is a graph that shows a comparison of transverse relaxivity values ($r_2$) for different magnetic nanoparticles.

We subsequently characterized the transverse relaxivity (r$_2$) of the Fe-core MNPs. To cross-examine the effects of the Ms and the size (d) of MNPs on r$_2$, we also prepared ferrite (Fe$_3$O$_4$) MNPs of different diameters. FIG. 7 is a comparison of the r$_2$ values for different MNPs, measured at Larmor frequency f0 (=ω0/2π)=20 MHz and T=300 K. Among ferrite MNPs, the r$_2$ rose with increased particle size (d). For a fixed particle size (d=16 nm), the r$_2$ values were proportional to Ms and correspondingly, Fe-core MNPs had higher values of r$_2$ than ferrite-based particles. Fe@MnFe$_2$O$_4$ MNPs assumed the highest r$_2$ due to its highest Ms; the r$_2$-enhancement over Fe$_3$O$_4$ or cross-linked iron oxide (CLIO) nanoparticles was greater than 2-fold and greater than 300-fold, respectively. We further analyzed the r$_2$ behavior of MNPS using an outer-sphere model that takes into account the water diffusion in r$_2$ calculation. In short, with sufficiently small particle size, the diffusional motion of water molecules is fast enough to average out the magnetic fields from MNPs, and the $r_2$ in this regime is $\sim d^2 \cdot Ms$. Indeed, the observed $r_2$ values were highly compatible with theoretical values, which 1) validated the approach for enhancing $r_2$, by increasing particle size and the magnetization; and 2) verified that the MNPs were well-dispersed without aggregation to be in the motional-averaging regime (d less than 23 nm for Fe@MnFe$_2$O$_4$.

To understand the unusual magnetic properties of Fe@MFe$_2$O$_4$ MNPs, we performed two different levels of magnetic simulations:

Hysteresis loops were calculated for an ensemble of MNPs, which included exploring the effects of thermally-activated reversal of magnetization.

The configuration of magnetization vectors in a single particle was analyzed through micromagnetic simulations.

The results revealed a novel mechanism of magnetization within Fe@MFe$_2$O$_4$ MNPs. In this mechanism, the Fe core (diameter=12 nm) exhibits single-domain, ferromagnetic behavior with appreciable coercivity, while the ferrite shell has a superparamagnetic nature and is easily magnetized at low external magnetic fields (Hext). When these two components (core and shell) are combined together, the coercivity is reduced as the shell leads the initial magnetization at low Hext, but the hysteresis loss associated with the core is retained at higher Hext. The proposed model consequently explains the magnetic behavior observed in Fe@MFe$_2$O$_4$ MNPs in temperature and external field dependent magnetization.

Example 4

Surface Modification and Conjugation with Biotin or Antibody

Fe@MnFe$_2$O$_4$ MNPs were suspended in 10 mL chloroform, and 50 µL triethylamine was added. DMSA (50 mg) in 10 mL DMSO was injected into the nanoparticle solution. The mixture was shaken for 6 hours at 40° C. until it gradually turned heterogeneous, and precipitated down by centrifugation (3,000 rpm, 10 minutes). The precipitate was carefully washed with ethanol to remove excess DMSA, and dispersed in 10 mL ethanol using a homogenizer. DMSA (50 mg) in 10 mL DMSO was added again to the nanoparticle-ethanol solution, and the whole process was repeated. The final precipitate was dispersed in 50 mL H$_2$O. The DMSA-treated nanoparticles were eventually terminated with sulfhydryl (—SH) and unbound carboxylic acid; both chemical functional groups can be used to conjugate specific targeting moieties. The number of sulfhydryl groups per nanoparticle was about 50 as determined by Ellman's reagent (Pierce Biotechnology). To conjugate DMSE-treated Fe@MnFe$_2$O$_4$ MNPs with (+)biotin-hydrazide (Aldrich), amide bonds were formed on the Fe@MnFe$_2$O$_4$ MNPs using carboxylic acid and amine groups were formed in biotin using NHS/EDC chemical reactions.

The DMSA-treated Fe@MnFe$_2$O$_4$ MNPs (25 mg) were dispersed in 10 mL H$_2$O, followed by the addition of NHS (3.5 mg), EDC (5 mg), and biotin (1 mg). The mixture was shaken for 3 hours at room temperature. The conjugated Fe@MnFe$_2$O$_4$ MNPs were then precipitated down (12,000 rpm, 20 minutes) and washed three times with H$_2$O. To conjugate antibodies, the antibodies were first rendered thiol active by attaching maleimide functional groups. The antibodies were then dissolved (anti-HER2/neu: Herceptin, 6 mg/mL) in 1 mL PBS buffer and the pH was adjusted to 8.2 by adding 0.1 M NaHCO$_3$, and 1 mg sulfo-SMCC. The mixture was incubated for 30 minutes at 37° C. The maleimide-active antibody was then purified with a PD-10 desalting column (GE Healthcare Bio-Sciences) and immediately combined with the DMSA treated nanoparticles (5 mg/mL). The mixture was shaken for 6 hours at 4° C., after which it was purified using Sephadex G-100 (DNA grade, GE Healthcare Bio-Sciences). The number of antibodies per nanoparticle was about 10 as determined using bicinchoninic acid assays (BCA protein assay kit, Pierce Biotechnology).

Example 5

Surface Modification of MNPs and Cytotoxicity Test

Figure 8:
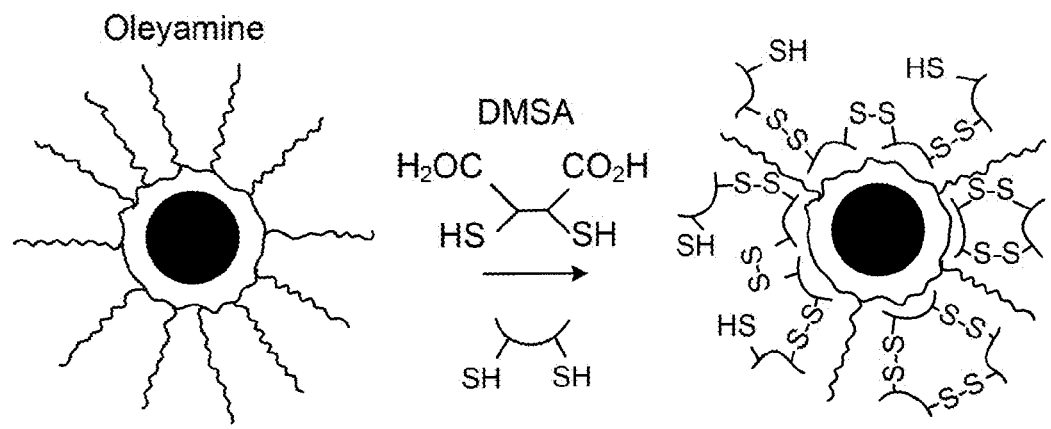
FIG. 8 is a schematic representation of a Fe@MnFe$_2$O$_4$ magnetic nanoparticle before and after coating with dimercapto-succinic acid (DMSA) for conjugation with targeting moieties.

To transfer as-synthesized, hydrophobic Fe@MnFe$_2$O$_4$ MNPs to aqueous buffers, we modified the particle surface with 2,3-dimercaptosuccinic acid (DMSA) through ligand exchange. DMSA contains two carboxylic acid (—COOH) and two sulfhydryl (—SH) groups. When mixed with MNPs, the carboxylic acid initially forms direct chelating bonds with the Fe@MnFe$_2$O$_4$ MNP surface. FIG. 8 is a schematic diagram of Fe@MnFe$_2$O$_4$ MNP coated with DMSA for conjugation with targeting moieties. The DMSA coating is stabilized via intermolecular disulfide cross-linking among DMSA molecules. Employing this method, we could reliably render the Fe@MnFe$_2$O$_4$ MNPs water-soluble.

To conjugate targeting moieties to the particles, we utilized the terminal sulfhydryl or carboxylic acid functional groups. For instance, we could couple biotin molecules to the carboxylic acid groups of DMSA using NHS/EDC chemistry (N-hydroxysuccinimide, NHS; N-ethyl-N'-(3-(dimethylamino)propyl)carbodiimide, EDC). Antibodies, separately modified with a maleimide functional group, were conjugated to the sulfhydryl groups via disulfide bonding (Section VIII). We subsequently tested for potential cytotoxicity associated with the DMSA-coated Fe@MnFe$_2$O$_4$ MNPs. Normal (3T3 fibroblast) and cancer (HCT 116) cells were cultured for 24 hours, following introduction of different quantities of MNPs. The cellular viability was then analyzed with a 3-(4,5-dimethylthiazol-2-yl)-2,5-diphenyltetrazolium (MTT) bromide assay (see Section VII). No acute cytotoxic effects were observed, which confirmed the biocompatibility of both the DMSA-coated and the magnetic materials.

Example 6

Demonstration of Biological Applications Including Avidin Titration and Cellular Assay To demonstrate the biological applications of Fe@MFe$_2$O$_4$ MNPs, we used the particles to sense biological markers with the NMR-based diagnostic platform (DMR, diagnostic magnetic resonance). DMR sensing is based on the change of transverse relaxation time ($\Delta T2$) when detection targets in samples are recognized by MNPs. For molecular targets (e.g. proteins), the DMR assay employs the phenomenon of magnetic relaxation switching, in which MNPs are cross-linked with target molecules to form nanometer-scale clusters. For larger objects (e.g., bacteria, mammalian cells), targets are labeled with MNPs, and unbound particles are removed prior to measurements. For both assay configurations, the detection sensitivity is commensurate with the r2 of MNPs.

Figure 9:
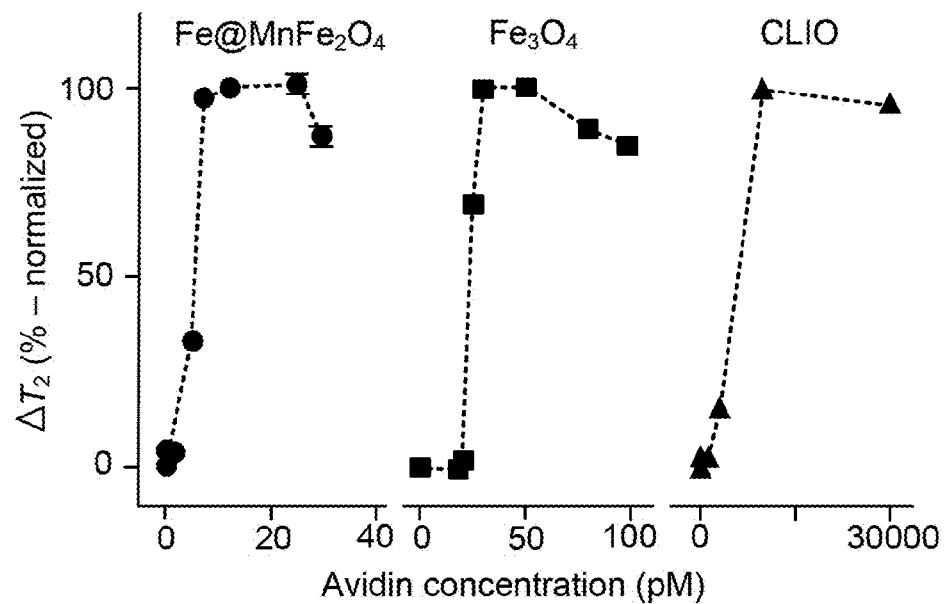
FIG. 9 is a graph that shows normalized ΔT2 versus avidin concentration for several types of nanoparticles.

Initially, we evaluated the sensing capacity of Fe@MFe$_2$O$_4$ MNPs in molecular detection, using biotin-avidin interaction as a model. Titration experiments with biotinylated MNPs showed avidin dose-dependent T2 changes. FIG. 9 shows a graph of normalized ΔT2 versus avidin concentration for several types of nanoparticles. Among the other types of MNPs, Fe@MnFe$_2$O$_4$ showed the highest sensitivity by detecting about 1.5 pM of avidin; the DMR assay is as sensitive as ELISA but with the added advantage of requiring much smaller samples (about 1 μl) and shorter assay times (less than 30 min).

Avidin titration: Avidin (ImmunoPure Avidin #21121; Pierce Biotechnology) was dissolved in PBS. Samples were prepared by mixing various amounts of avidin to biotinylated Fe@MnFe$_2$O$_4$ MNPs. Following 15 minutes of incubation at 37° C., the T2 values of samples were measured on 1 μL samples using the miniaturized Nuclear Magnetic Resonance (NMR) system previously reported in "Chip-NMR biosensor for detection and molecular analysis of cells," (Lee et al., Nat. Med. 14, pp. 869-874 (2008)). Carr-Purcell-Meiboom-Gill pulse sequences were used with the following parameters: echo time (TE), 4 msec; repetition time (TR), 6 sec; the number of 180° pulses per scan, 500; the number of scans, 8. As a reference, ΔT2 was calculated using the T2 values of samples without avidin. All measurements were performed in triplicate and data were displayed as mean±standard error.

Figure 10A:
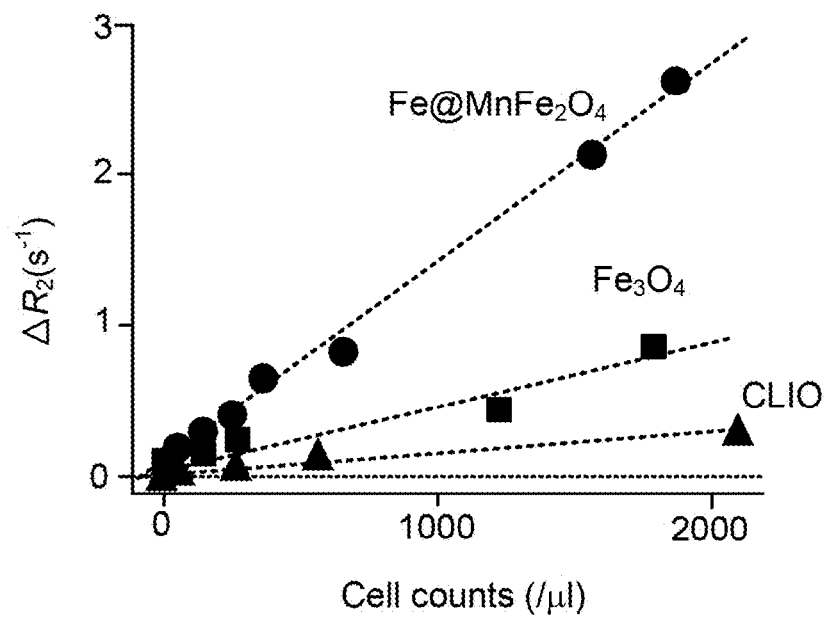
FIG. 10A is a graph that shows relaxation rate per cell concentration for several types of MNPs.
Figure 10B:
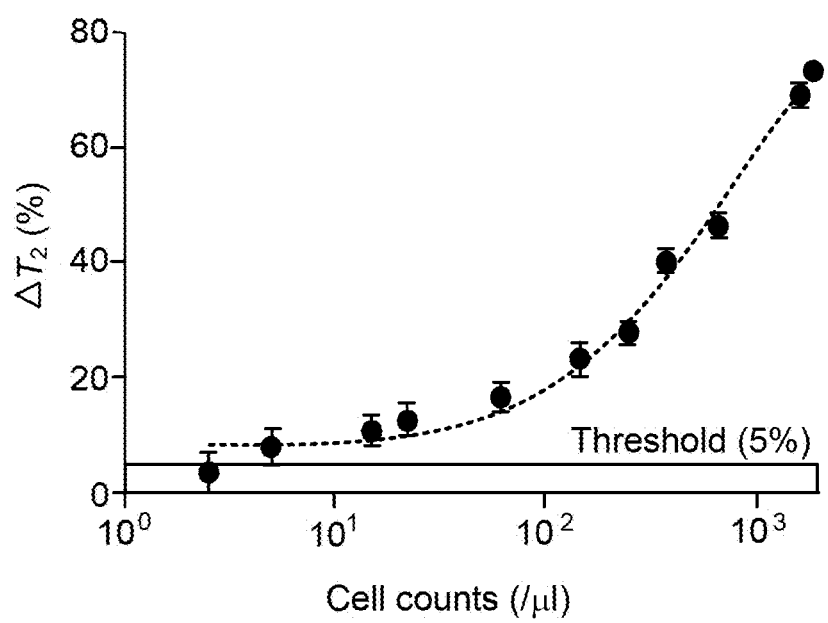
FIG. 10B is a graph that shows normalized ΔT2 versus cell concentration for Fe@MnFe$_2$O$_4$ MNPs.

For cellular detection, we tagged cancer cells (SkBr3) with MNPs conjugated to antibodies that target a tumor marker (HER2). Following the MNP-incubation, the cellular relaxivities, defined as the relaxation rate (1/T2) per cell concentration, were found to be proportional to the r2 of the MNPs. FIG. 10A is a graph that shows relaxation rate per cell concentration for several types of MNPs. Consequently, Fe@MnFe$_2$O$_4$ produced the most pronounced ΔT2, which permitted target detection close to the level of single cells. FIG. 10B is a graph that shows normalized ΔT2 versus cell concentration for Fe@MnFe$_2$O$_4$ MNPs.

Human SkBr3 breast cancer cells were cultured in vendor-recommended media and maintained at 37° C. in a humidified atmosphere of 5% CO2 in air. At confluence, the cells were incubated with Fe@MnFe$_2$O$_4$ MNPs conjugated with HER2/neu antibodies for 10 minutes at 37° C. Reference samples were prepared without targeting. All samples were triple-washed via centrifugation (1,000 rpm, 5 minutes), resuspended in PBS, and serially diluted. The cell concentration in a sample was determined using a hemocytometer. The same miniaturized NMR system and the pulse sequences (described previously) were used to obtain T2 measurements.

Example 7

Magnetic Resonance Imaging (MRI)

Fe@MFe2O4 MNPs were evaluated for use as MRI imaging agents. A comparative study of phantoms confirmed the use of Fe@MnFe2O4 for enhancing contrast. For example, compared to the widely-used CLIO nanoparticles, Fe@MnFe$_2$O$_4$ was able to produce the same signal changes at about 10 times lower doses. We also performed preliminary in vivo imaging studies. We intravenously injected a variety of MNPs [cross-linked iron oxide (CLIO), Fe$_3$O$_4$, and Fe@MnFe$_2$O$_4$] into mice, while keeping the same metal dose (10 mg [metal]/kg). We then obtained T2-weighted images at different time points using a 7 T MRI machine (Pharmascan, Bruker). Taken at 3 hours post-injection, the images verified that the contrast enhancement was indeed commensurate with the r2 value of each type of MNPs.

Figure 11:
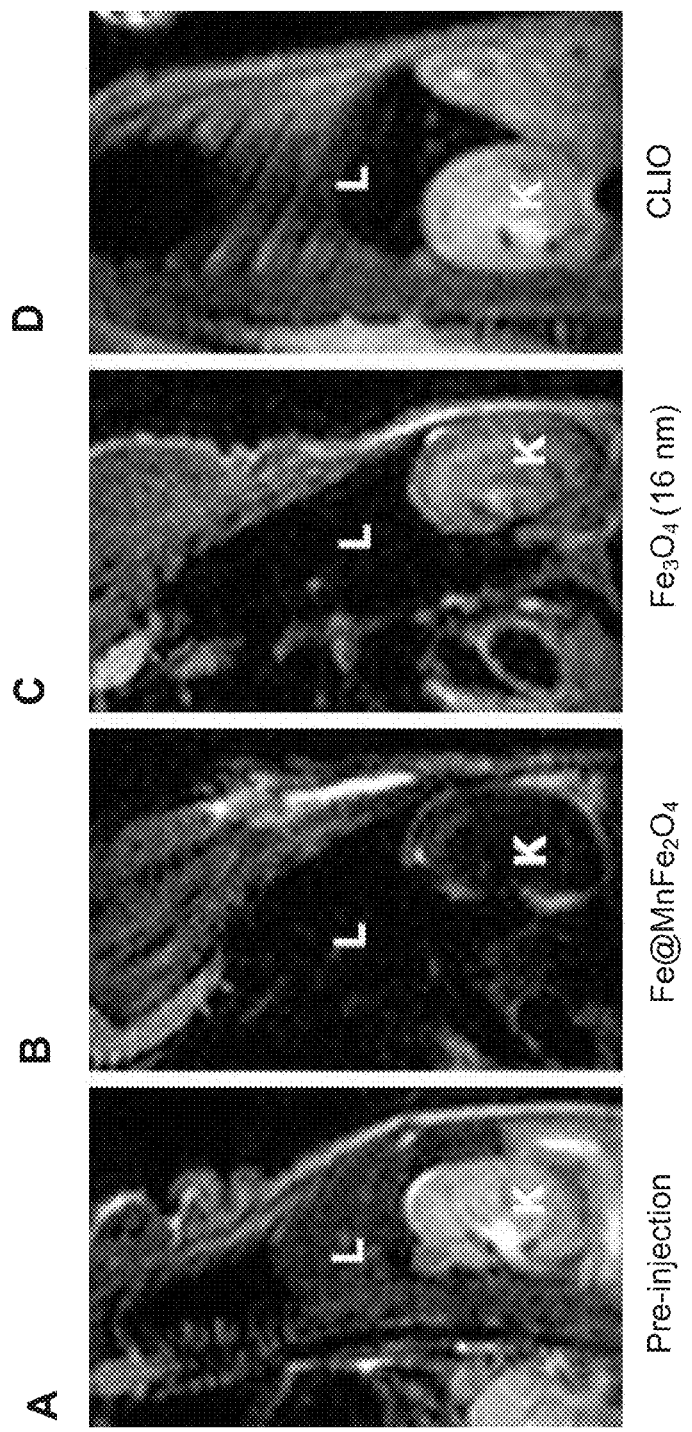
FIGS. 11A to 11D are MRI images for different magnetic nanoparticles.

FIG. 11A is an MRI image of organs prior to the injection of MNPs. FIGS. 11B to 11D are MRI images of organs in which different MNPs have been injected. The letter "L" in the images identifies the location of the liver whereas the letter "K" in the images identifies the location of the kidney. Fe@MnFe2O4 MNPs (FIG. 11B) resulted in the most significant darkening, which supports the potential utility of Fe@MnFe2O4 MNPs as an efficient imaging agent. In organs containing phagocytic cells such as liver, spleen, or bone marrow, the peak signal changes occurred at around 3 hours after intravenous administration, consistent with an hour long blood half-life. At early time points, most organs including kidneys showed considerable darkening due to vascular perfusion. These changes all returned to baseline within 24 hours.

The imaging study was performed using a 4.7 T and a 7.0 T scanner (Bruker) and a volume coil in birdcage design (Rapid Biomedical, Germany). To determine r2, phantoms consisting of Fe@MnFe$_2$O$_4$ MNPs with different metal concentrations were prepared and T2 values were measured using the following spin echo parameters: TE=10 msec; TR=2000 msec; matrix 256×256; number of 180° pulses per scan=16. For mouse imaging, Fe@MnFe$_2$O$_4$ MNPs (in PBS) were injected intravenously with a metal dose of 10 mg [metal]/kg via the tail vein. The animal was anesthetized with isoflurane (5% induction, 1.5% maintenance) in the mixed gas of N$_2$O and O$_2$ (7:3). T2-weighted images were then obtained using the following parameters: TE=36 msec; TR=2420 msec; flip angle 90°; matrix 128×128; field of view 4×4 cm$^2$, slice thickness 1 mm.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A nanoparticle comprising:
   a solid ferromagnetic core;
   a super-paramagnetic shell on a surface of and surrounding the magnetic core, wherein the super-paramagnetic shell has a thickness between about 0.5 nm and about 3 nm.
2. The nanoparticle of claim 1, wherein the nanoparticle has a diameter greater than or equal to about 2 nm.
3. The nanoparticle of claim 1, wherein the ferromagnetic core has a core diameter in a range of about 1 nm to about 15 nm.
4. The nanoparticle of claim 1, wherein the ferromagnetic core comprises Fe, Co, Ni, FePt or SmCo.
5. The nanoparticle of claim 1, wherein the super-paramagnetic shell comprises an oxide of a magnetic material.
6. The nanoparticle of claim 1, wherein the super-paramagnetic shell comprises a dopant material.
7. The nanoparticle of claim 6, wherein the dopant material comprises a metal selected from the group consisting of Mn, Co, Ni, Zn, and ZnMn.

8. The nanoparticle of claim 1, further comprising a coating on the super-paramagnetic shell, wherein the coating is configured to increase the aqueous solubility of the nanoparticle.

9. The nanoparticle of claim 8, wherein the coating comprises 2,3-dimercaptosuccinic acid (DMSA).

10. The nanoparticle of claim 1, further comprising a coating on the super-paramagnetic shell, wherein the coating is configured to bind the nanoparticle to a target molecule.

11. The nanoparticle of claim 1, further comprising a dextran polymer coating on the super-paramagnetic shell.

* * * * *